United States Patent [19]

Hess et al.

[11] Patent Number: 5,149,833
[45] Date of Patent: Sep. 22, 1992

[54] PROCESS FOR PREPARING D,L-LACTIDE

[75] Inventors: Joachim Hess, Bingen; Klaus R. Muller, Ingelheim; Manfred Muller, Bickenbach, all of Fed. Rep. of Germany

[73] Assignee: Boehringer Ingelheim GmbH, Ingelheim am Rhein, Fed. Rep. of Germany

[21] Appl. No.: 650,507

[22] Filed: Feb. 5, 1991

Related U.S. Application Data

[62] Division of Ser. No. 529,022, May 25, 1990, Pat. No. 5,011,946.

[30] Foreign Application Priority Data

May 26, 1989 [DE] Fed. Rep. of Germany ....... 3917178

[51] Int. Cl.⁵ ............................................ C07D 319/12
[52] U.S. Cl. .................................................... 549/274
[58] Field of Search ......................................... 549/274

[56] References Cited

U.S. PATENT DOCUMENTS

| | | | |
|---|---|---|---|
| 4,797,468 | 1/1989 | De Vries | 549/274 |
| 4,983,745 | 1/1991 | Muller et al. | 549/274 |
| 4,990,222 | 2/1991 | Aigner et al. | 549/274 |

FOREIGN PATENT DOCUMENTS 0275581 7/1988 European Pat. Off. .
0261362 10/1988 Fed. Rep. of Germany .

Primary Examiner—C. Warren Ivy
Assistant Examiner—Amelia A. Owens
Attorney, Agent, or Firm—David E. Frankhouser; Daniel Reitenbach; Alan R. Stempel

[57] ABSTRACT

An improved process for the preparation of D,L-Lactide which can be used directly in polymerization reactions.

7 Claims, No Drawings

PROCESS FOR PREPARING D,L-LACTIDE

This is a division of application Ser. No. 529,022, filed May 25, 1990, now U.S. Pat. No. 5,011,946.

The invention relates to a process for preparing D,L-lactide which can be used in reactions of polymerisation without any further purification.

Polymers of D,L-lactide are used in a variety of applications, e.g. in the manufacture of biodegradable surgical aids, such as surgical suturing material, orthopaedic pins, vessel implants, etc. In the production of the polymers, depending on the desired properties, the D,L-lactide may be reacted on its own to form the poly-D,L-lactide or reacted with other monomers to produce the corresponding copolymers. The properties of the resulting polymers are influenced considerably by the purity of the D,L-lactide used.

Hitherto, the only processes known for the production of D,L-lactide are those in which racemic lactic acid is used as starting material.

However, these processes have a number of disadvantages, of which one serious one is the fact that a proportion of at least 50% of undesirable meso-lactide will automatically be obtained when racemic lactic acid is reacted to produce D,L-lactide. The meso-lactide can only be separated from the D,L-lactide by the use of complicated, expensive and wasteful methods (repeated recrystallisation from various solvents, extraction, sublimation).

A method developed by E. Jungfleisch and M. Godchot [C. R. Hebd. Séances Acad. Sci. 142 (1906) 639] starts from D- and L-lactide which after co-crystallisation yield the desired D,L-lactide. However, this method suffers from the disadvantage that the highly flammable diethylether has to be used as solvent in a weight ratio of 70:1 (in industrial processes the ratio of solvent to solids is usually in the range from 2:1 to 10:1). Another disadvantage of this method is that the D,L-lactide thus produced cannot be polymerised without additional laborious purification.

The objective of the present invention is therefore to provide a process which makes it possible to produce D,L-lactide under industrial conditions of manufacture which can be polymerised to yield poly-D,L-lactide or the corresponding copolymers without the need for any additional purification.

According to the invention, this objective is achieved by carrying out the co-crystallisation of D-lactide and L-lactide in solvents or mixtures of solvents which permit the azeotropic distillation of water, oligomers and residual lactic acid and any solvent residues which might have a detrimental effect on the subsequent reaction of polymerisation and then allowing the D- and L-lactide to crystallise out together and isolating the co-crystallate.

By contrast to the methods for producing D,L-lactide which have been used hitherto, the method according to the invention yields a D,L-lactide which is produced under industrial conditions and can be used in reactions of polymerisation without any further purification.

The starting materials used are $D(+)$-lactide and $L(-)$-lactide.

The solvent and solvent mixtures used are solvents which are capable of forming an azeotropic mixture with water and which do not have a detrimental effect on co-crystallisation. Examples of such azeotropes are known to those skilled in the art [Timmermans, The Physico-Chemical Constants of Binary Systems in Concentrated Solutions, Interscience, New York N.Y., 1959-1960 and the Supplement 1965 ff; Azeotropic Data, Advances in Chemistry, Series No. 6 and No. 35, American Chemical Society, Washington D.C., 1952 and 1962].

Preferably, toluene is used as the solvent.

The solvent or solvents used is or are conveniently dried, e.g. azeotropically, before the co-crystallisation.

$L(-)$-lactide and $D(+)$-lactide are expediently each dissolved in some of the solvent or solvent mixture, with the exclusion of moisture. Preferably, $L(-)$-lactide and $D(+)$-lactide are each dissolved in half the total quantity of solvent or solvent mixture used.

The solutions are conveniently filtered while hot and then mixed together. Then some of the solvent is removed, optionally under reduced pressure. The residual solution is cooled, preferably to a temperature of about 20° C. when toluene is used as solvent. The D,L-lactide which crystallises out is freed from solvent, preferably by centrifugation, and dried, optionally under reduced pressure.

The D,L-lactide produced in this way can be polymerised without any further purification.

The Example which follows serves to illustrate the invention without restricting it.

EXAMPLE

Preparation of the D,L-lactide 900 liters of toluene are azeotropically dried by distilling off about 100 liters under normal pressure. 135 kg of $L(-)$-lactide and 135 kg of $D(+)$-lactide are each dissolved in 400 liters of azeotropically dried toluene at a temperature in the range from 40°-70° C. The two solutions are filtered while hot and then mixed together. From the resulting mixture, 160 liters of toluene are distilled off under a pressure of 50 mbar. The remaining solution is cooled to 20° C., at which stage the D,L-lactide crystallises out. The D,L-lactide is centrifuged and dried in vacuo under a pressure of 10 to 15 mbar.

244.0 kg (90.4% of theory) of D,L-lactide are obtained.

Polymerisation of D,L-lactide

A sample of the D,L-lactide thus obtained is polymerised with a catalyst known from the prior art (such as tin(II) octanoate). The values of the inherent viscosity of D,L-lactide polymers produced in this way are in the range of $\eta_{inh}=4$ to 5 dl/g (measured in chloroform at 25° C.).

What is claimed is:

1. A process for preparing D,L-lactide which comprises
   a) dissolving D-lactide in a first volume of a solvent or a mixture of solvents capable of forming an azeotrope with water, to produce a first solution;
   b) filtering the first solution;
   c) dissolving L-lactide in a second volume of the solvent or mixture of solvents, to produce a second solution; d) filtering the second solution; e) combining the filtered first solution and the filtered second solution, to produce a starting solution; f) concentrating the starting solution, to produce a residual solution; g) cooling the residual solution until a crystalline precipitate of D,L-lactide forms; h) separating the crystalline precipitate from the remainder of the residual solution; and i) drying the crystalline precipitate.

2. A process as recited in claim 1 wherein the solvent is toluene.

3. A process as recited in claim 2 wherein steps a)–d) are each conducted at a temperature between about 40° C. to about 70° C.

4. A process as recited in claim 3 wherein steps f) and i) are each conducted at a pressure below atmospheric pressure.

5. A process as recited in claim 4 wherein in step f, the starting solution is concentrated by evaporation.

6. A process as recited in claim 1 wherein the first volume is about equal to the second volume.

7. A process as recited in claim 6 wherein the concentration of D-lactide in the first solution is about equal to the concentration of L-lactide in the second solution.

* * * * *